United States Patent [19]

Manghisi et al.

[11] Patent Number: 4,584,321
[45] Date of Patent: Apr. 22, 1986

[54] 3-(3-HYDROXYBUTOXY)-1-BUTANOL IN PHARMACEUTICAL COMPOSITIONS

[75] Inventors: Elso Manghisi; Aldo Salimbeni, both of Milan, Italy

[73] Assignee: Istituto Luso Farmaco d'Italia S.p.A., Milan, Italy

[21] Appl. No.: 603,134

[22] Filed: Apr. 23, 1984

[30] Foreign Application Priority Data

May 30, 1983 [IT] Italy ................................ 21352 A/83

[51] Int. Cl.⁴ .............................................. A61K 31/08
[52] U.S. Cl. ...................................... 514/722; 568/680
[58] Field of Search ........................ 424/343; 568/680; 514/722

Primary Examiner—Stanley J. Friedman
Attorney, Agent, or Firm—Bucknam and Archer

[57] ABSTRACT 3-(3-Hydroxybutoxy)-1-butanol having formula II and its stereoisomers and optical isomers, at the pure state, are described

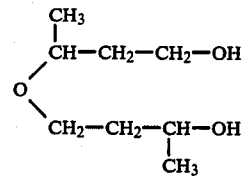

Processes for the purification of II and for the preparation of a pure diastereoisomer of II are described. Pharmaceutical compositions containing as the active ingredient compound II alone or combined with the isomeric ethers 4-(3-hydroxybutoxy)-2-butanol I and 3-(3-hydroxy-1-methylpropoxy)-1-butanol III.

2 Claims, No Drawings

3-(3-HYDROXYBUTOXY)-1-BUTANOL IN PHARMACEUTICAL COMPOSITIONS

The "Dihydroxydibutylether", pharmacologically active compound available in the international markets, consists of a mixture of isomeric hydroxylated ethers. The preparation of such a mixture can be carried out according to one of the different methods described in literature for the preparation of aliphatic ethers from primary or secondary alcohols; for instance, it can be obtained by heating 1,3-butandiole in the presence of catalytic amounts of $H_2SO_4$. In these conditions, a mixture of products deriving from the reaction of the primary and secondary alcoholic moieties with other alcoholic groups of the same kind or of the other one, as well as products deriving from dehydration or oxydation reactions of 1,3-butandiole or of the ethers obtained from condensation, is obtained.

By fractional distillation of the reaction mixture, the mixture of isomeric hydroxylated ethers contamined in low percentage by variable amounts of numerous by-products not easily identifiable, but detectable in the gas-chromathographic analysis, is obtained. The isomeric hydroxylated ethers mixture cannot be separated into the single components, unless by using particular methods suitable for analytical purposes, but not economically applicable in industrial stage. According to the researches performed by the applicant, the hydroxylated ethers present in the mixture "Dihydroxydibutylether" have been identified and structures I, that is 4-(3-hydroxybutoxy)-2-butanol, II, i.e. 3-(3-hydroxybutoxy)-1-butanol and III, i.e. 3-(3-hydroxy-1-methylpropoxy)-1-butanol, have been assigned.

These ethers are naturally present as racemic mixtures and "meso" forms:

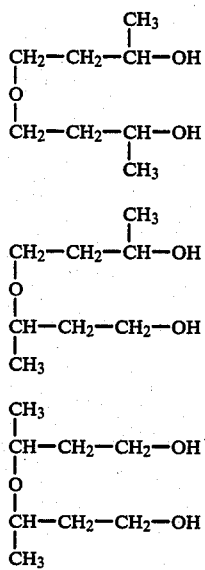

According to the Belgian Patent No. 709,336, in the applicant's name, compound I is prepared by treating 1,3-butandiole with sodium hydride and p.toluensulphochloride in dioxane at 50°-60°. In these conditions the primary hydroxy groups react selectively; nevertheless the formation of small amounts of the II isomer cannot be completely avoided.

In the Japanese Patents Nos. 80838 and 80839, in the name of Nippon Zohki Pharm. Co., the preparation of compound III is on the contrary described by means of etherification of α-methyl-γ-methoxypropanol with $H_2SO_4$ and subsequent dealkylation with hydroiodic acid of the obtained methoxyether. This method, because of the low selectivity of the used reagents, does not allow to obtain a product having an high purity degree. The compound III is generically described to possess colagogue and spasmolytic properties.

The preparation of compound II, on the contrary, has not been described in literature. Only small amounts, for analytical purpose, have been isolated by T. Fujirrani, H. Tsuji, S. Saki, *Polymer J.* 9, 553 (1977), by alkaline hydrolysis of polyether carbonate polymer.

No pharmacological activity is of course reported for this compound.

On the other side it is known that the single components of an isomeric mixture, as well as the single racemic forms of a compound having several asymmetric centers, can exert different or more favourable pharmacological actions (both as far as side effects and action potency or else are concerned) in comparison with the isomeric mixtures or with the racemic forms mixture.

The present invention refers to compound (II), as well as to diastereoisomers and optically active forms thereof, endowed with particular pharmacological properties; a method for the preparation of (II) allowing the separation both from the impurities, comprising unsaturated dehydration products, and from (I) and (III) isomers, present in the mixture commercially known as "Dihydroxydibutylether", and which are in turn isolated and purified; an isolation method of the racemic forms of (II), as well as pharmaceutical compositions based on compound II alone or in combination. The elimination of the impurities comprising unsaturated dehydration products is carried out by means of repeated extractions with aliphatic hydrocarbons (such as hexane, heptane, ligroine and so on) of "Dihydroxydibutylether", commercial mixture, diluted or not in a solvent immiscible with said hydrocarbons.

The separation of the II isomer from the I and III isomers is carried out taking advantage of the different reactivity of the primary and secondary hydroxy groups with respect to trityl chloride according to the used experimental conditions. By operating in fact according to the classical tritylation method consisting in reacting an alcohol with triphenylmethyl chloride in the presence of pyridine (preferably also used as a solvent), at temperatures ranging from the room temperature up to 100°, the reaction is not selective and both primary and secondary hydroxy groups (even by operating in reagent's defect) are tritylated. On the contrary, by reacting triphenylmethylchloride in an apolar solvent (such as $CH_2Cl_2$ and so on) at room temperature, in the presence of triethylamine and of catalytic amounts of 4-dimethylaminopyridine, the reaction is surprisingly characterized by an high selectivity. In these conditions, in fact, only the primary hydroxy groups present in compounds II and III, react, forming respectively the monotritylether IV and the ditritylether V, while the secondary hydroxy groups present in compounds I and II remain unchanged:

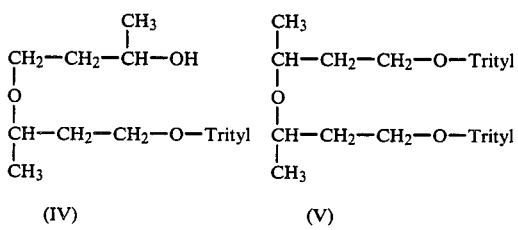

4-(3-Hydroxybutoxy)-2-butanol (I), unchanged, can be therefore easily extracted at this step from the reaction mixture by means of repeated washings with water, and recovered from the latter, with an high purity degree, by distillation.

The subsequent separation of ditritylether (V) from monotritylether (IV) is obtained according to the invention by using the remarkable, unforeseeable solubility differences of the two derivatives in linear or branched aliphatic alcohols (such as $CH_3OH$, EtOH, propanole, isopropanole and so on) in percentages ranging from 10 to 90. As a consequence, the treatment of the compounds IV and V mixture with said alcohols, or with said alcohols-aliphatic hydrocarbons mixture, allows to obtain the ditritylether (V) as a crystalline solid and to separate it from the monotritylether (IV), remained in solution, by filtration. At last, the acid hydrolysis of the compound IV and V so purified, carried out for instance with an inorganic acid such as HCl, HBr or an organic one such as acetic acid, in a solvent such as dioxane or methylene chloride, gives respectively the II and III isomers at the pure state.

The above described method proves to be industrially advantageous for the following reasons: (1) easy of operations; (2) use of cheap reagents, with the exception of triphenylmethyl chloride, which can be however recovered as triphenylmethylcarbinole and then, following halogenation, used again; (3) possibility to obtain in pure form, besides II, also the I and III isomers.

The so obtained compound II comprises the mixture of the two racemic forms (3 R*, 3'R*) and (3 R*, 3'S*). One of the two isomers, having a net defined configuration, can be isolated at the pure state by treatment of such a mixture with an aromatic acyl halide (such as benzoylchloride, p.nitrobenzoylchloride, 2,4-dinitrobenzoylchloride, and so on), separation of the acyl-derivative as pure racemate, fractional crystallization, and hydrolysis of the racemic acyl derivative. By treatment, for instance, of the racemic mixture II with p.nitrobenzoylchloride in pyridine and crystallization from methanol of the obtained product, the bis-p.nitrobenzoate of a pure racemic compound of II is isolated, from which the pure racemic compound itself can be isolated by acid (for instance in dioxane/water, in the presence of HCl or $H_2SO_4$) or basic (for example with KOH in EtOH) hydrolysis.

The pure racemic II itself can also be obtained by treatment of the isomers I, II, III mixture commercially known as "Dihydroxydibutylether", with an excess of p.nitrobenzoylchloride, repeated fractional crystallization of the mixture of the obtained derivatives and hydrolysis of the bis-p.nitrobenzoate of the above isolate pure racemic compound.

The compound II (as well as its diastereoisomers and its optically active forms) in addition to an hepatoprotective and choleretic activity, proves to be active in the prophylaxis and in the therapy of biliary calculosis and of the dyslipidemia and possesses a marked diuretic activity.

It can be administered by parenteral and oral route by means of suitable pharmaceutical formulations such as vials, syrups, drops, gelatine pills, tablets, granules.

The daily dose may range from 50 to 2000 mg. In such formulations the compound II can be the active principle alone or in combination with the I and III isomers, also pharmacologically active, in variable ratios and particularly in the 13:60:27 ratio (for I, II, III respectively).

The following examples further illustrate the invention without limiting it in any way.

The boiling and melting points are not correct. The identity of the compounds and their purity have been determined by elemental analysis (C, H, N) and by IR, UV, $H^1$ and $^{13}C$-NMR spectroscopical analysis.

EXAMPLE 1

Purification of "Dihydroxydibutylether"

(a) 35 Kg of 1,3-butandiole were heated at 170° for 1 h in the presence of catalytic amounts of $H_2SO_4$ 9N (240 ml). After elimination under vacuo of the water formed during the reaction, the reaction mixture was cooled, neutralized with dil. NaOH and then distilled under vacuo to give 9 kg of "Dihydroxydibutylether"; p.eb. 156°–161° C./20 mm.

According to the gas-chromatographic analysis (Carbowax 20 M column) it proved to consist of the mixture of three isomers ethers I, II, and III and impurities mainly due to unsaturated dehydration products.

(b) The mixture was heated and treated, with stirring, with the same volume of petroleum ether. The hydrocarbon phase was discarded and the residue was treated again with petroleum ether. The operation was repeated until when the unsaturated products were no longer present according to the gas-chromatographic analysis.

The product was distilled under vacuo: p.eb. 156°–161° C./20 mm.

EXAMPLE 2

Reaction with triphenylmethylchloride 96 g of 4-dimethylaminopyridine, 3.6 kg of triethylamine and 6 kg of triphenylmethyl chloride were added to a solution of 2.44 kg of "Dihydroxydibutylether" (purified as described in the example 1) in 54 liters of $CH_2Cl_2$. The mixture was left under stirring for 48 h at room temperature, distilled water was then added and the phases were separated. The organic phase was washed several times with water, the aqueous phases were collected, evaporated under vacuo and the residue was treated with acetone and ethyl ether. The separated organic and inorganic salts were filtered and the solution was evaporated. The oily residue was distilled in vacuo to give 165 g of 4-(3-hydroxybutoxy)-2-butanol I, as mixture of racemic form and "meso" form; boiling point 156°–161° C./20 mm; $^{13}C$-NMR ($CDCl_3$): δ23.5 (C-1 and C-4'), 38.4 (C-3 and C-2'), 65.8 (C-2 or C-3'), 66.0 (C-2 or C-3'), 68.8 (C-4 or C-1'), 69.0 (C-4 or C-1').

By treatment of 32 g of I (as isomers mixture) dissolved in 30 ml of pyridine with 84 g of p.nitrobenzoylchloride, 30 g of bis-p-nitrobenzoate of one of the two isomeric forms of I (m.p. 84°–86° C., from EtOH) were isolated, according to the methods reported in the example 4 (part a)), with the configuration not determined, from which 9 g of 4-(3-hydroxybutoxy)-2-butanol I (racemic or "meso" form) were obtained by alkaline hydrolysis, according to the methods reported in the Example 5; boiling point 156°–161° C./20 mm; $^{13}$C-NMR (CDCl$_3$): 23.5 (C-1 and C-4'), 38.4 (C-3 and C-2'), 66.0 (C-2 or C-3'), 69.0 (C-4 or C-1'). The organic phase, after drying on Na$_2$SO$_4$, was filtered and evaporated. The oily residue was dissolved with warming in EtOH.

By slow crystallization a mixture of ditrityl derivative of 3-(3-hydroxy-1-methylpropoxy)-1-butanol (compound V) and of triphenylcarbinole precipitated. The ethanolic mother liquors were evaporated and dissolved in hexane. After 24 h, some more ditrityl derivative (V) precipitated, in admixture with triphenylcarbinole, which was filtered and collected with the previous one. The hexanic mother liquors were treated with neutral alumina and left under stirring for 2 h. The alumina was filtered and washed several times with hexane. The alumina was suspended in EtOH, filtered and washed with EtOH. The ethanolic solutions were collected and evaporated. The residue (3.7 kg) corresponds to the monotrityl derivative of 3-(3-hydroxybutoxy)-1-butanol (compound IV) and was used as such for the subsequent reaction.

EXAMPLE 3

3-(3-Hydroxybutoxy)-1-butanol (II, racemic mixture)

0.37 l of 37% HCl and 0.37 l of 1:1 HCl were added to a solution of 3.7 kg of monotrityl derivative of 3-(3-hydroxybutoxy)-1-butanol (compound IV), obtained as described in the example 2, in 14 l of dioxane. The mixture was heated at 100° C. for 1 h. After cooling, it was diluted with water. The precipitated triphenylcarbinole was filtered off and the aqueous solution was neutralized with diluted sodium hydroxide and then evaporated. The solid residue was mixed with acetone and ethyl ether. The inorganic salts were filtered and the solution was evaporated. By distillation in vacuo of the oily residue, 0.76 kg of 3-(3-hydroxybutoxy)-1-butanol (II) (as racemic mixture) were obtained: b.p. 156°–161° C./20 mm; $^{13}$C-NMR (CDCl$_3$) δ19.6 (C-4), 38.8 (C-2'), 39.2 (C-2), 59.3 and 59.5 (C-1), 65.9 and 66.5 (C-3'), 66.2 and 66.5 (C-1'), 73.8 and 74.1 (C-3).

EXAMPLE 4

Bis-p-nitrobenzoate of 3-(3-hydroxybutoxy)-1-butanol (pure racemic compound)

(a) 627 g of p-nitrobenzoyl chloride were added in portions to a solution of 246 g of 3-(3-hydroxybutoxy)-1-butanol (II, racemic mixture, prepared as described in the example 3) in 2.5 ml of anhydrous pyridine. The mixture was heated to 125° C. for 1 h. After cooling, the mixture was poured in iced water, acidified with diluted HCl to pH 3 and extracted several times with CH$_2$Cl$_2$.

The separated organic phase was washed first with a saturated NaHCO$_3$ solution and then with water to neutrality. After drying on Na$_2$SO$_4$, the mixture was filtered and evaporated. The oily residue was made to solidify by treatment with CH$_3$OH and then crystallized from said solvent to give bis-p-nitrobenzoate of 3-(3-hydroxy-butoxy)-1-butanol II (pure racemic compound); m.p. 77°–78° C. (b) 265 g of p-nitro-benzoyl chloride were added in portions to a solution of 100 g of "Dihydroxydibutylether", purified as described in the example 1, in 1.25 l of anhydrous pyridine. The mixture was heated to 125° for 1 h, and then worked out as previously reported. Repeated crystallizations from CH$_3$OH of the obtained solid yielded the bis-p-nitrobenzoate of the above 3-(3-hydroxybutoxy)-1-butanol II (pure racemic); m.p. 77°–78° C.

EXAMPLE 5

3-(3-Hydroxybutoxy)-1-butanol (II, pure racemic)

44 g of KOH were added to a solution of 125 g of bis-p-nitrobenzoate of 3-(3-hydroxybutoxy)-1-butanol (pure racemic), prepared as described in the example 4, in 1.9 l of EtOH. The mixture was refluxed for 1 h, then cooled, filtered and evaporated. The residue was treated with a NaCl saturated water solution and extracted several times with CH$_2$Cl$_2$.

The collected organic phases were washed with a saturated NaHCO$_3$ solution and with H$_2$O. After drying on Na$_2$SO$_4$, the solvent was evaporated. The residue was distilled to give 3-(3-hydroxybutoxy)-1-butanol II (pure racemic), as colourless oil; b.p. 156°–161° C./20 mm; $^{13}$C-NMR (CDCl$_3$): δ19.6 (C-4), 23.5 (C-4'), 38.8 (C-2'), 39.2 (C-2), 59.3 (C-1), 66.0 (C-3'), 66.2 (C-1'), 73.9 (C-3).

EXAMPLE 6

3-(3-Hydroxy-1-methylpropoxy)-1-butanol, III 30 ml of 1:1 HCl and 30 ml of 37% HCl were added to a solution of 300 g of ditrityl derivative of 3-(1-methyl-3-hydroxypropoxy)-1-butanol III (compound V), obtained as described in example 2, in 1.8 l of dioxane. The mixture was heated to 100° C. for 1 h, then cooled and diluted with water. The precipitated triphenylcarbinole was filtered and the aqueous solution, after neutralization with diluted NaOH, was evaporated.

The residue, after elimination of the inorganic salts by treatment with ether, was distilled to give 3-(3-hydroxy-1-methylpropoxy)-1-butanol (III, racemic and "meso" form mixture): b.p. 156°–161° C./20 mm; $^{13}$C-NMR (CDCl$_3$): 19.9 and 21.4 (C-4 and C-1''), 39.6 (C-2 and C-2'), 59.0 and 59.2 (C-1 and C-3'), 70.5 and 71.6 (C-3 and C-1').

The racemic and "meso" forms can be separated by means of fractional crystallization from methyl ethyl ketone of the above ditrityl derivative and subsequent hydrolysis of the separated pure compounds (racemic ditrityl derivative: m.p. 149°–151° C.; "meso" ditrityl derivative; m.p. 130°–132° C.) in the above reported conditions: III (racemic): b.p. 156°–161° C./20 mm; $^{13}$C-NMR (CDCl$_3$): δ19.9 (C-4 and C-1''), 39.6 (C-2 and C-2'), 59.2 (C-1 and C-3'), 70.5 (C-3 and C-1'); III ("meso"): b.p. 156°–161° C./20 mm; $^{13}$C-NMR (CDCl$_3$): δ21.4 (C-4 and C-1''), 39.6 (C-2 and C-2'), 59.0 (C-1 and C-3'), 71.6 (C-3 and C-1').

EXAMPLE 7

| Pharmaceutical formulation: syrup | |
|---|---|
| 3-(3-Hydroxybutoxy)-1-butanol | g 7 |
| Sugar | g 42 |
| Methyl p.hydroxybenzoate | g 0.15 |
| Propyl p.hydroxybenzoate | g 0.015 |
| Purified water to | ml 100 |

EXAMPLE 8

| Pharmaceutical formulation: capsules | |
|---|---|
| 3-(3-Hydroxybutoxy)-1-butanol | mg 150 |

| Pharmaceutical formulation: capsules | |
|---|---|
| Soft gelatine capsule | mg 100 |

EXAMPLE 9

| Pharmaceutical formulation: drops | |
|---|---|
| 3-(3-Hydroxybutoxy)-1-butanol | g 35 |
| Absolute ethyl alcohol | g 35 |
| Anetole | g 1.5 |
| Purified water to | ml 100 |

EXAMPLE 10

| Pharmaceutical formulation: capsules | |
|---|---|
| 3-(3-Hydroxybutoxy)-1-butanol | mg 100 |
| 4-(3-Hydroxybutoxy)-2-butanol | mg 50 |
| Soft gelatine capsule | mg 100 |

EXAMPLE 11

| Pharmaceutical formulation: syrup | |
|---|---|
| 3-(3-Hydroxybutoxy)-1-butanol | g 4.2 |
| 3-(3-Hydroxy-1-methylpropoxy)-1-butanol | g 1.89 |
| 4-(3-Hydroxybutoxy)-2-butanol | g 0.91 |
| Sugar | g 42 |
| Methyl p.hydroxybenzoate | g 0.15 |
| Propyl p.hydroxybenzoate | g 0.015 |
| Purified water to | ml 100 |

EXAMPLE 12

| Pharmaceutical formulation: capsules | |
|---|---|
| 3-(3-Hydroxybutoxy)-1-butanol | mg 90 |
| 3-(3-Hydroxy-1-methylpropoxy)-1-butanol | mg 40.5 |
| 4-(3-Hydroxybutoxy)-2-butanol | mg 19.5 |
| Soft gelatine capsule | mg 100 |

EXAMPLE 13

| Pharmaceutical formulation: drops | |
|---|---|
| 3-(3-Hydroxybutoxy)-1-butanol | g 21 |
| 3-(3-Hydroxy-1-methylpropoxy)-1-butanol | g 9.45 |
| 4-(3-Hydroxybutoxy)-2-butanol | g 4.55 |
| Absolute ethyl alcohol | g 35 |
| Purified water to | ml 100. |

We claim:

1. A pharmaceutical composition useful as an hepatoprotective agent, choleretic agent in the propylaxis and therapy of biliary calculosis and dyslipidemia which contains as the active ingredient 3-(3-hydroxybutoxy)-1-butanol formula II,

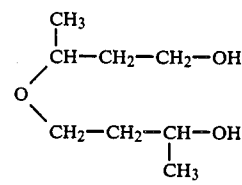

stereoisomers and optical isomers thereof and at least one pharmaceutically acceptable carrier, said compound of formula II being of such a degree of purity that its bis-p-nitrobenzoate derivative has a m.p. of 78°–79° C. and a spectrum $^{13}$C-NMR (CDCl$_3$): δ19.6 (C-4), 23.4 (C-4'), 38.8 (C-2'), 39.2 (C-2), 59.3 (C-1), 66.0 (C-3'), 66.2 (C-1'), 73.9 (C-3), the amount of said active ingredient being such in at least one unit dose to administer 50–2000 mg daily to a patient in need of such treatment.

2. A pharmaceutical composition useful as an hepatoprotective agent, choreretic agent in the prophylaxis and therapy of biliary calculosis and dylipidemia, which contains as the active ingredients the compounds I, II and III:

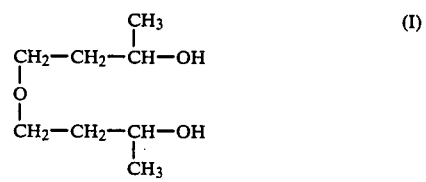

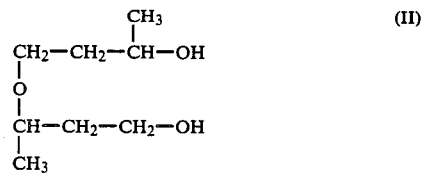

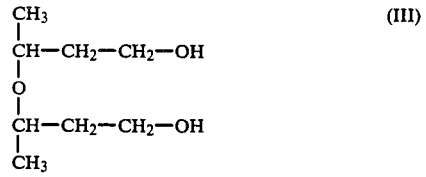

in the 60:13:27 ratio for compounds II, I and III respectively, and at least one pharmaceutically acceptable excipient, the amount of said active ingredients being such in at least one unit dose to administer 50–2000 mg daily to a patient in need of such treatment.

* * * * *